US012558449B2

(12) United States Patent
Hirata et al.

(10) Patent No.: US 12,558,449 B2
(45) Date of Patent: Feb. 24, 2026

(54) GAS SENSOR DEVICE, INFORMATION PROCESSING APPARATUS, AND ODOR PRESENTATION SYSTEM

(71) Applicant: Sony Interactive Entertainment Inc., Tokyo (JP)

(72) Inventors: Shinichi Hirata, Kanagawa (JP); Yuichi Machida, Kanagawa (JP); Takeshi Asano, Tokyo (JP); Yoichi Nishimaki, Kanagawa (JP); Takao Maruyama, Kanagawa (JP); Yumi Ueda, Chiba (JP)

(73) Assignee: Sony Interactive Entertainment Inc., Tokyo (JP)

( * ) Notice: Subject to any disclaimer, the term of this patent is extended or adjusted under 35 U.S.C. 154(b) by 345 days.

(21) Appl. No.: 18/248,568

(22) PCT Filed: Oct. 22, 2020

(86) PCT No.: PCT/JP2020/039669
§ 371 (c)(1),
(2) Date: Apr. 11, 2023

(87) PCT Pub. No.: WO2022/085144
PCT Pub. Date: Apr. 28, 2022

(65) Prior Publication Data
US 2023/0372571 A1 Nov. 23, 2023

(51) Int. Cl.
*A61L 9/12* (2006.01)
*G01N 27/407* (2006.01)
(Continued)

(52) U.S. Cl.
CPC ............ *A61L 9/125* (2013.01); *G01N 27/407* (2013.01); *G01N 2030/025* (2013.01);
(Continued)

(58) Field of Classification Search
CPC ............................ A61L 9/125; G01N 27/407; G01N 2030/025; G01N 30/20; G01N 30/88; G01N 30/32
(Continued)

(56) References Cited

U.S. PATENT DOCUMENTS

| | | | | |
|---|---|---|---|---|
| 5,012,671 A | * | 5/1991 | Yagawara | ............... G01N 27/12 73/31.06 |
| 10,532,278 B2 | * | 1/2020 | Nishimaki | ............ G09F 19/005 |

(Continued)

FOREIGN PATENT DOCUMENTS

| | | | | |
|---|---|---|---|---|
| EP | 4101810 A1 | * | 12/2022 | ............. B01D 46/10 |
| JP | 2136738 A | | 5/1990 | |

(Continued)

OTHER PUBLICATIONS

Bruins et al., Enabling a transferable calibration model for metal-oxide type electronic noses, Sensors and Actuators B 188 (2013) 1187-1195 (Year: 2013).*

(Continued)

*Primary Examiner* — Stephanie E Bloss
*Assistant Examiner* — Kevin C Butler
(74) *Attorney, Agent, or Firm* — Kilpatrick Townsend & Stockton LLP

(57) ABSTRACT

Provided is a gas sensor device including a plurality of sensitive members and a measuring instrument. The plurality of sensitive members have respective sensitive materials that react to molecules present in the air and targeted for measurement. The measuring instrument independently measures the respective reactions of the plurality of sensitive members to the molecules.

18 Claims, 5 Drawing Sheets

(51) Int. Cl.

| | | |
|---|---|---|
| *G01N 30/02* | (2006.01) | |
| *G01N 30/20* | (2006.01) | |
| *G01N 30/32* | (2006.01) | |
| *G01N 30/88* | (2006.01) | |

(52) U.S. Cl.
    CPC ............. *G01N 30/20* (2013.01); *G01N 30/32* (2013.01); *G01N 30/88* (2013.01); *G01N 2030/8881* (2013.01)

(58) Field of Classification Search
    USPC ....................................................... 73/23.42
    See application file for complete search history.

(56) References Cited

U.S. PATENT DOCUMENTS

| | | | | |
|---|---|---|---|---|
| 10,905,788 | B2 | 2/2021 | Nishimaki | |
| 10,942,940 | B2 | 3/2021 | Hirata | |
| 2018/0144033 | A1* | 5/2018 | Hirata | A63F 13/217 |
| 2018/0318461 | A1* | 11/2018 | Nishimaki | A61L 9/122 |
| 2018/0318706 | A1* | 11/2018 | Nishimaki | G09F 19/00 |

FOREIGN PATENT DOCUMENTS

| | | | | | |
|---|---|---|---|---|---|
| JP | H02136738 | A | * 5/1990 | ............. | G01N 27/12 |
| JP | 3289555 | A | 12/1991 | | |
| JP | H03289555 | A | * 12/1991 | ............. | G01N 27/12 |
| JP | 2877822 | B2 | * 4/1999 | ............. | G01N 27/12 |
| JP | 2003250877 | A | * 9/2003 | | |
| JP | 2014153135 | A | * 8/2014 | | |
| JP | 2019046495 | A | * 3/2019 | ........... | A63F 13/212 |
| JP | 2019048071 | A | * 3/2019 | ............... | A61L 9/12 |
| KR | 20180048702 | A | * 5/2018 | ............. | G01N 27/64 |
| KR | 20190114009 | A | * 10/2019 | ............. | G01N 27/12 |
| WO | WO-2016199452 | A1 | * 12/2016 | ........... | A63F 13/212 |
| WO | WO-2017094284 | A1 | * 6/2017 | ............. | A63F 13/28 |
| WO | WO-2019102654 | A1 | * 5/2019 | ............. | G01N 27/12 |
| WO | WO-2022196708 | A1 | * 9/2022 | | |

OTHER PUBLICATIONS

International Search Report for corresponding PCT Application No. PCT/JP2020/039669, 6 pages, dated Dec. 28, 2020.

* cited by examiner (a)

(b)

(c)

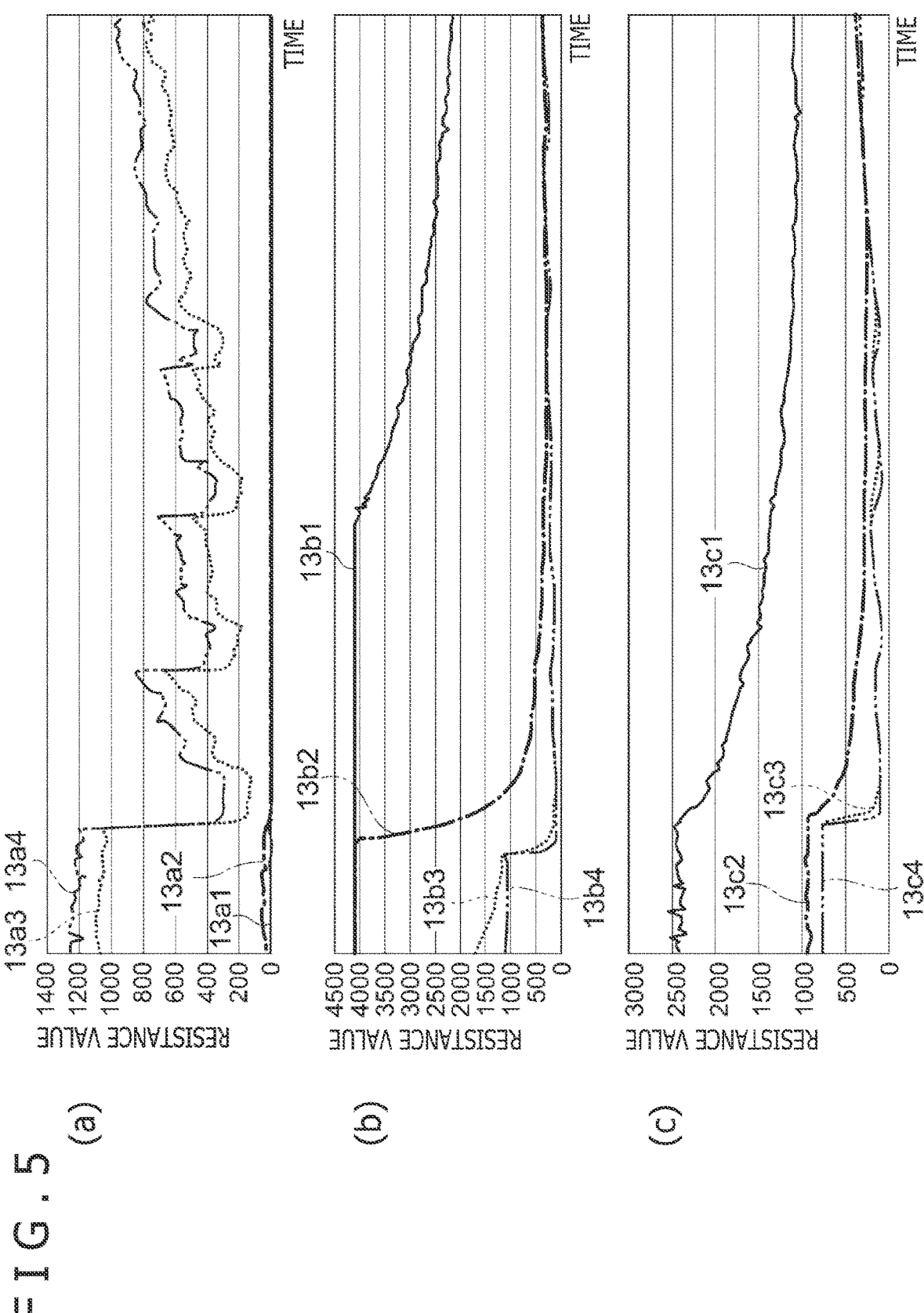
F I G . 5

GAS SENSOR DEVICE, INFORMATION PROCESSING APPARATUS, AND ODOR PRESENTATION SYSTEM

TECHNICAL FIELD

The present invention relates to a gas sensor device, an information processing apparatus, and an odor presentation system.

BACKGROUND ART

The use of an odor presentation apparatus for presenting a specific odor to a user is now being considered for the purpose of allowing the user to experience a realistic sensation, for example, in a video game. The odor presentation apparatus presents an odor to the user by releasing molecules causing the odor (odor molecules) into the air.

SUMMARY

Technical Problem

When the above-mentioned odor presentation apparatus presents an odor, it is conceivable that a gas sensor device capable of detecting odor molecules in a gas is used, for example, to check whether the odor is actually presented or to check the intensity of the presented odor. However, particularly in a case where the odor presentation apparatus presents various types of odors, an efficient method for detecting such various types of odors has not sufficiently been studied.

The present invention has been made in view of the above circumstances. An object of the present invention is to provide a gas sensor device, an information processing apparatus, and an odor presentation system that are able to detect various types of odors.

Solution to Problem

A gas sensor device according to an aspect of the present invention includes a plurality of sensitive members and a measuring instrument. The plurality of sensitive members have respective sensitive materials that react to molecules present in the air and targeted for measurement. The measuring instrument independently measures the respective reactions of the plurality of sensitive members to the molecules.

An information processing apparatus according to an aspect of the present invention includes an acquisition section and an identification section. The acquisition section acquires respective results of measurements of the plurality of sensitive members from the gas sensor device. Based on the acquired results of the measurements, the identification section identifies a type and intensity of an odor included in the air.

An odor presentation system according to an aspect of the present invention includes an odor presentation apparatus, a gas sensor device, and an information processing apparatus. The odor presentation apparatus is able to present a plurality of types of odors. The gas sensor device includes a plurality of sensitive members and a measuring instrument. The plurality of sensitive members have respective sensitive materials that react to molecules present in the air and targeted for measurement. The measuring instrument independently measures the respective reactions of the plurality of sensitive members to the molecules. The information processing apparatus includes an acquisition section and an identification section. The acquisition section acquires respective results of measurements of the plurality of sensitive members in a situation where an odor is presented by the odor presentation apparatus. Based on the acquired results of the measurements, the identification section identifies a type and intensity of the odor presented by the odor presentation apparatus.

BRIEF DESCRIPTION OF DRAWINGS

FIG. 5 illustrates diagrams of another example of the result of the measurement by the gas sensor device.

DESCRIPTION OF EMBODIMENT

An embodiment of the present invention will now be described in detail with reference to the accompanying drawings.

Figure 1:
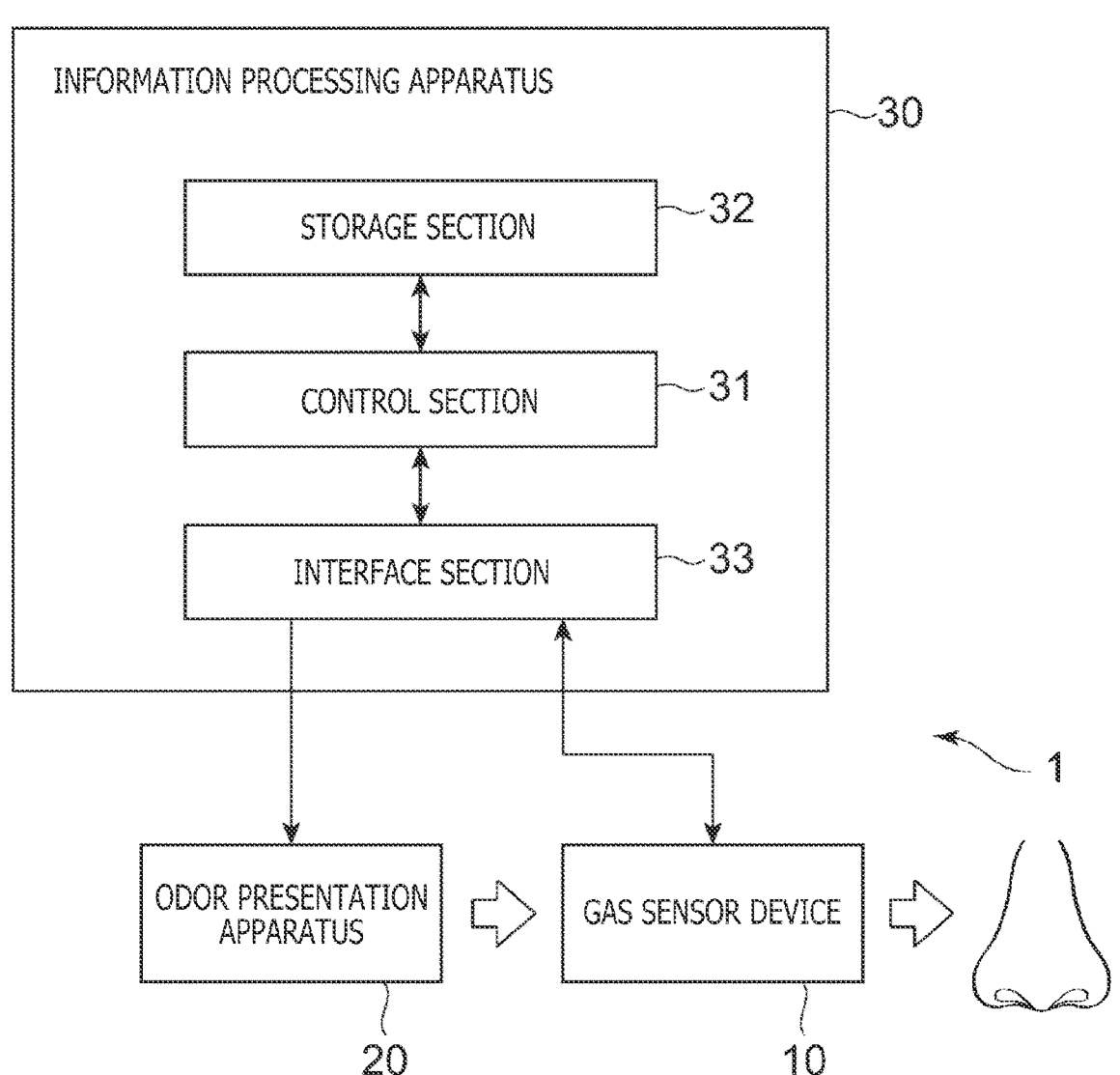
FIG. 1 is an overview diagram illustrating an odor presentation system according to an embodiment of the present invention.

FIG. 1 is an overview diagram illustrating an odor presentation system 1 according to the embodiment of the present invention. As illustrated in FIG. 1, the odor presentation system 1 includes a gas sensor device 10, an odor presentation apparatus 20, and an information processing apparatus 30.

The gas sensor device 10 is a device for detecting molecules that are present in the air and that are targeted for measurement (here, the molecules are odor molecules causing an odor). By using a result of measurement by the gas sensor device 10, the information processing apparatus 30 identifies the type and intensity of the odor presented by the odor presentation apparatus 20.

Figure 2:
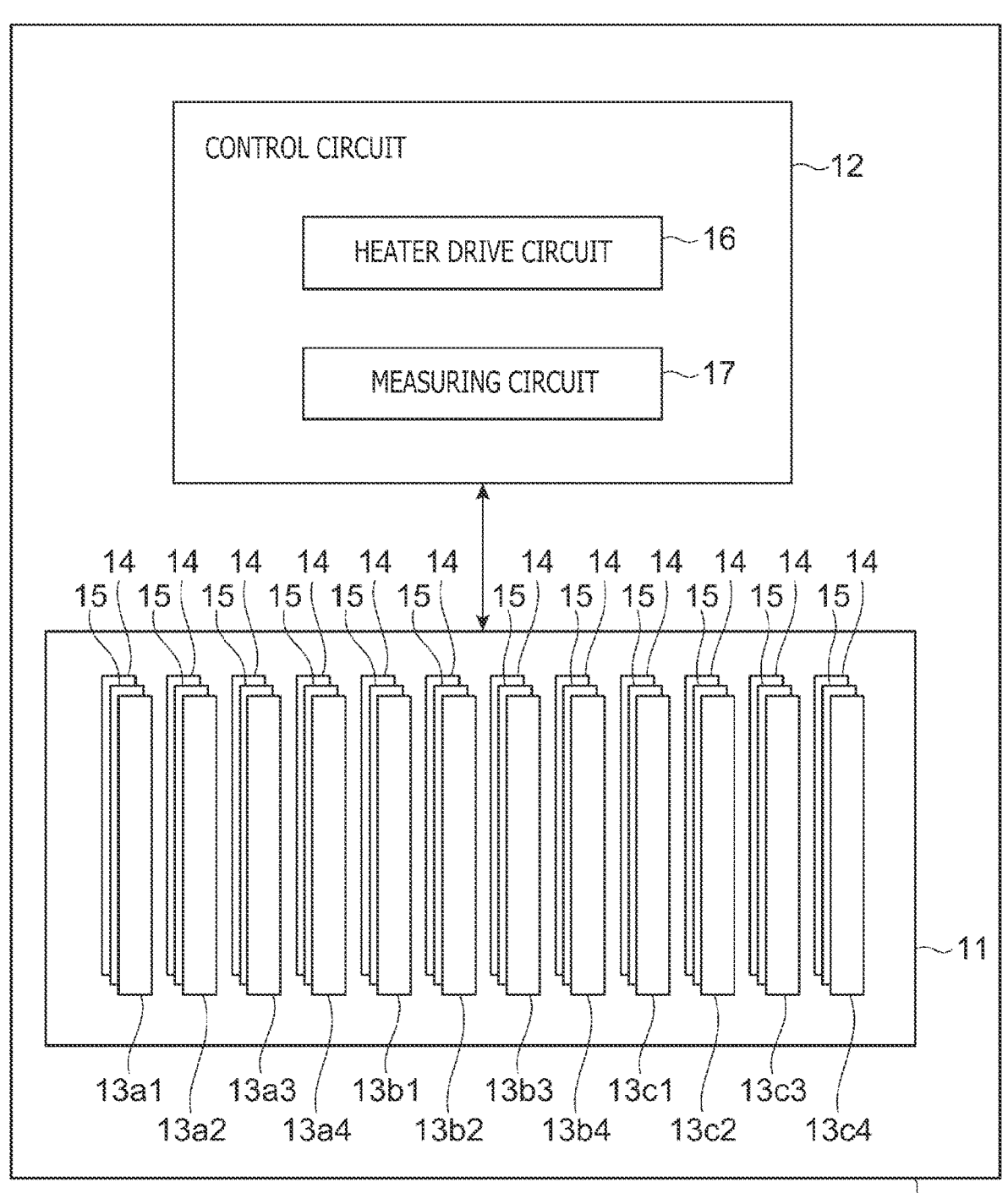
FIG. 2 is a diagram illustrating a configuration of a gas sensor device according to the embodiment of the present invention.

FIG. 2 is a schematic configuration diagram illustrating the gas sensor device 10. As illustrated in FIG. 2, the gas sensor device 10 includes a sensor section 11 and a control circuit 12. The sensor section 11 may be, for example, a microelectromechanical systems (MEMS) die. The control circuit 12 may be, for example, an application-specific integrated circuit (ASIC) die. Further, the sensor section 11 and the control circuit 12 may be configured together as a single integrated circuit (IC) or as a single IC package.

The sensor section 11 is disposed at a place that can be reached by a gas containing odor molecules released by the odor presentation apparatus 20. A plurality of sensitive membranes (sensitive members) 13 are formed on the surface of the sensor section 11. The sensitive membranes 13 each include a sensitive material that reacts to the odor molecules targeted for measurement. In the present embodiment, it is assumed that the sensitive material used for each sensitive membrane 13 is an oxide semiconductor (MOx). For example, the sensitive membrane 13 is formed by applying and sintering an oxide semiconductor material to the surface of a silicon wafer serving as a base material for the sensor section 11. When the odor molecules in the air reach the sensor section 11 and adhere to the surface of the sensitive membrane 13, the sensitive membrane 13 reacts to the odor molecules to change its electrical characteristics. Accordingly, the gas sensor device 10 is able to detect the presence of odor molecules in the air by measuring a change in the resistance value of the sensitive membrane 13. Further, an increase in the amount of odor molecules present in the air increases the change in the resistance value of the sensitive membrane 13. Therefore, the information processing apparatus 30 is able to estimate the amount of odor molecules present in the air by referencing a measurement result indicating the amount of change in the resistance value.

In the example of FIG. 2, the plurality of sensitive membranes 13 are each shaped like an elongated rectangle when viewed from above, and are arranged side by side in a direction intersecting the direction of elongation. However, the shapes and arrangement mode of the sensitive membranes 13 are not limited to the above, and may be in various shapes and arrangement modes.

Further, a heater 14 is connected to each of the plurality of sensitive membranes 13. That is, the number of heaters 14 included in the sensor section 11 is the same as the number of sensitive membranes 13. By individually operating the heaters 14, the gas sensor device 10 is able to heat the plurality of sensitive membranes 13 independently. In general, when the temperature rises, the sensitive membranes 13 are more likely to react to the odor molecules, which results in an increase in sensor sensitivity. Therefore, when the odor molecules are to be measured, the gas sensor device 10 operates each heater 14 to heat each sensitive membrane 13 and raise its temperature.

Further, a temperature sensor 15 is disposed near each of the plurality of sensitive membranes 13. That is, the number of temperature sensors 15 included in the sensor section 11 is the same as the number of sensitive membranes 13 and the number of heaters 14. The temperature sensors 15 measure the temperatures of the sensitive membranes 13 disposed adjacent to the temperature sensors 15, and output the results of measurements to the control circuit 12.

The control circuit 12 functionally includes a heater drive circuit 16 and a measuring circuit 17. The heater drive circuit 16 receives an instruction from the information processing apparatus 30, and operates the individual heaters 14 according to the received instruction. As a result, the gas sensor device 10 can be controlled to heat the plurality of sensitive membranes 13 independently to different temperatures. Further, the heater drive circuit 16 receives the result of measurement by each temperature sensor 15 from the sensor section 11, and exercises feedback control to adjust the output of the corresponding heater 14 according to the received result of measurement. This allows the heater drive circuit 16 to heat each sensitive membrane 13 to a temperature that matches a target temperature based on the instruction from the information processing apparatus 30 with relatively high accuracy.

The measuring circuit (measuring instrument) 17 includes, for example, an analog-to-digital (AD) converter. The measuring circuit 17 receives, from the sensor section 11, an electrical signal reflecting the resistance value of each sensitive membrane 13, and measures the magnitude of the received electrical signal. Subsequently, the measuring circuit 17 transmits a digital signal indicative of the measured magnitude value to the information processing apparatus 30. The measuring circuit 17 independently measures the resistance values of the plurality of sensitive membranes 13. Further, the measuring circuit 17 repeatedly measures the resistance values of the respective sensitive membranes 13 at predetermined time intervals.

In the present embodiment, it is assumed that at least some of the sensitive membranes 13 included in the gas sensor device 10 are formed of different types of sensitive materials. For example, the type of reacting odor molecule and the degree of reaction (sensitivity) of each type of odor molecule vary from one type of sensitive material to another. Therefore, by including a plurality of types of sensitive membranes 13 having different types of sensitive materials, the gas sensor device 10 is able to measure a plurality of types of odor molecules.

Note that some types of sensitive materials have a characteristic, namely, a sensitivity, that allows their resistance values to be rapidly changed by specific chemical substances, whereas some other types of sensitive materials have such a wide sensitivity as to react to various types of chemical substances. The sensitive materials having the latter characteristic generally have poor selectivity for the chemical substances, and are probably unsuitable for the identification of the types of odor molecules. However, when a plurality of types of sensitive materials having the above-mentioned wide sensitivity are adopted to configure the gas sensor device 10 having a plurality of types of sensitive membranes 13, a later-described odor identification section 43 is able to increase the selectivity and identify various types of odor molecules by using, for example, a pattern analysis or machine learning method.

However, all of a plurality of sensitive membranes 13 included in the gas sensor device 10 need not be formed of different types of sensitive materials. At least some of the sensitive membranes 13 may be formed of sensitive materials of the same type. As mentioned earlier, when measuring the odor molecules, the gas sensor device 10 is able to let the heaters 14 change the temperatures of the individual sensitive membranes 13 to different temperatures. Further, even the sensitive membranes 13 having sensitive materials of the same type differ in the response speed and sensitivity of reaction to the odor molecules when the temperatures of the sensitive membranes 13 are different from one another. Accordingly, the gas sensor device 10 measures a plurality of sensitive membranes 13 formed of sensitive materials of the same type, in a state where the sensitive membranes 13 are heated to different temperatures. This makes it possible to measure the odor molecules from several perspectives, widen the overall measurement range of the gas sensor device 10, and measure a variety of types of odor molecules.

In a concrete example described below, it is assumed that the gas sensor device 10 includes three types of sensitive membranes 13 formed of sensitive materials of different types, and includes four sensitive membranes 13 of each type. That is, the gas sensor device 10 according to the present embodiment includes a total of twelve sensitive membranes 13. Four sensitive membranes 13 formed of a first type of sensitive material are hereinafter referred to, respectively, as the sensitive membranes 13*a*1, 13*a*2, 13*a*3, and 13*a*4. Similarly, sensitive membranes 13 formed of a second type of sensitive material are hereinafter referred to, respectively, as the sensitive membranes 13*b*1, 13*b*2, 13*b*3, and 13*b*4, and sensitive membranes 13 formed of a third type of sensitive material are hereinafter referred to, respectively, as the sensitive membranes 13*c*1, 13*c*2, 13*c*3, and 13*c*4.

The odor presentation apparatus 20 is an apparatus for presenting a specific type of odor to a user. More specifically, the odor presentation apparatus 20 presents an odor, for example, by releasing a gas containing specific odor molecules. Note that various types of mechanisms may be used for the purpose of allowing the odor presentation apparatus 20 to present an odor.

Further, it is assumed in the present embodiment that the odor presentation apparatus 20 is able to present a plurality of types of odors to the user. For example, the odor presentation apparatus 20 may include a plurality of different cartridges of a built-in type in which different types of fragrances are sealed. According to an instruction from the information processing apparatus 30, the odor presentation apparatus 20 releases a gas containing a fragrance that is sealed in a cartridge specified by the instruction. Accordingly, the information processing apparatus 30 is able to allow the odor presentation apparatus 20 to present different types of odors according to the processing to be performed by the information processing apparatus 30.

Further, it is assumed that the odor presentation apparatus 20 includes a mechanism for allowing the user to replace a cartridge. Accordingly, by allowing the user to replace the cartridge with another cartridge in which a different type of fragrance is sealed, the odor presentation apparatus 20 is able to change the odor that can be presented. Moreover, in a case where the amount of fragrance sealed in a cartridge is decreased, the fragrance can be supplemented by replacing the cartridge with a new one. Note that, as described later, a situation where the amount of fragrance in a cartridge is decreased can be detected by the information processing apparatus 30 through the use of the result of measurement by the gas sensor device 10.

Additionally, it is assumed in the present embodiment that the odor presentation apparatus 20 is able to adjust the intensity of the odor to be presented to the user. More specifically, according to an instruction from the information processing apparatus 30, the odor presentation apparatus 20 changes, for example, the amount of fragrance to be released, for the purpose of adjusting the intensity of the odor to be presented.

Note that, in order to enable the gas sensor device 10 to accurately measure the odor presented by the odor presentation apparatus 20, it is desirable that the gas sensor device 10 and the odor presentation apparatus 20 be disposed in such a manner as to maintain a substantially constant distance between them. The reason is that a change in the distance between the gas sensor device 10 and the odor presentation apparatus 20 causes a change in the intensity of the odor to be measured by the gas sensor device 10. Therefore, for example, the gas sensor device 10 may be built in the odor presentation apparatus 20 or may securely be attached to a housing of the odor presentation apparatus 20. It is also desirable that the gas sensor device 10 be disposed between the odor presentation apparatus 20 and the nostrils of the user in order to efficiently present an odor to the user and to properly measure the air containing the odor presented to the user. Block arrows in FIG. 1 represent the flow of a gas released by the odor presentation apparatus 20, and indicate that the gas sensor device 10 is disposed in the middle of a flow path through which the gas released from the odor presentation apparatus 20 moves towards and reach the nostrils of the user.

The information processing apparatus 30, which is a computer such as a home game console or a personal computer, includes a control section 31, a storage section 32, and an interface section 33 as depicted in FIG. 1.

The control section 31 includes at least one processor and performs various types of information processing according to a program stored in the storage section 32. Particularly in the present embodiment, the control section 31 outputs a control command to the odor presentation apparatus 20 for the purpose of presenting an odor, and identifies the result of odor presentation by using data indicative of a measurement result received from the gas sensor device 10. Concrete examples of the processing performed by the control section 31 will be described later.

The storage section 32 includes at least one memory device and stores a program to be executed by the control section 31 and data to be used by the program. The interface section 33 is an interface for establishing data communication with the gas sensor device 10 and the odor presentation apparatus 20. The information processing apparatus 30 receives data indicative of the measurement results from the gas sensor device 10 through the interface section 33 and transmits a control command for operating the odor presentation apparatus 20 to the odor presentation apparatus 20.

Figure 3:
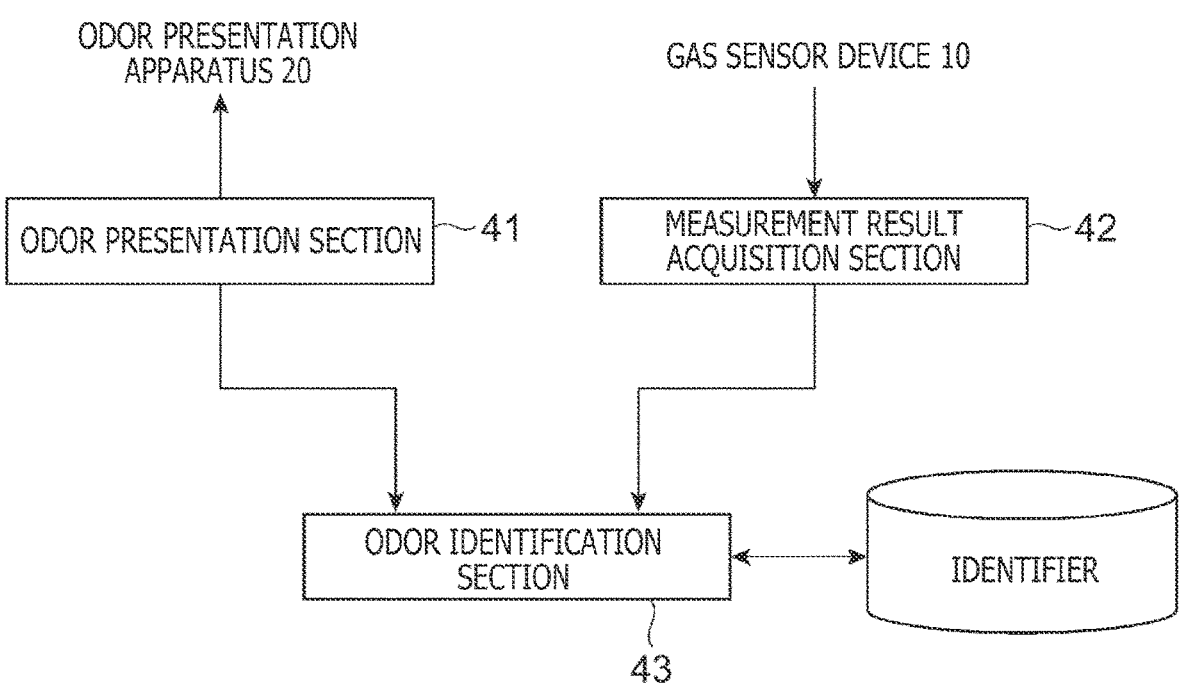
FIG. 3 is a functional block diagram illustrating an information processing apparatus according to the embodiment of the present invention.

FIG. 3 is a functional block diagram illustrating the functions implemented by the information processing apparatus 30. As depicted in FIG. 3, the information processing apparatus 30 functionally includes an odor presentation section 41, a measurement result acquisition section 42, and an odor identification section 43. The functions of these sections are implemented by causing the control section 31 to execute a program stored in the storage section 32. The program may be stored on a computer-readable information storage medium and supplied to the information processing apparatus 30 or may be supplied to the information processing apparatus 30 through a network such as the Internet.

The odor presentation section 41 causes the odor presentation apparatus 20 to present an odor by outputting a control command for operating the odor presentation apparatus 20. More specifically, according to the progress of processing performed by an application program, the odor presentation section 41 transmits an odor presentation command for specifying the type and intensity of an odor to the odor presentation apparatus 20.

The measurement result acquisition section 42 operates the gas sensor device 10 and acquires the result of measurement by the gas sensor device 10. More specifically, the measurement result acquisition section 42 first instructs the gas sensor device 10 to start measurement. In this instance, the measurement result acquisition section 42 also transmits, to the gas sensor device 10, heating instruction information indicating the degree to which each of the twelve sensitive membranes 13 should be heated. The heating instruction information may be information specifying the operating conditions (e.g., driving power) of the heaters 14 or information specifying a target temperature of each sensitive membrane 13.

Upon receiving the instruction for starting measurement, the control circuit 12 of the gas sensor device 10 operates the individual heaters 14 according to the contents of the heating instruction information to heat corresponding ones of the sensitive membranes 13. Then, in a state where the sensitive membranes 13 are heated according to the contents of the heating instruction information, the control circuit 12 measures the resistance values of the sensitive membranes 13 at predetermined time intervals, and transmits the results of measurements to the information processing apparatus 30.

The measurement result acquisition section 42 acquires time-series data indicative of temporal changes in the resistance values of the sensitive membranes 13, by successively receiving the results of measurements periodically transmitted from the gas sensor device 10. In this instance, the measurement result acquisition section 42 acquires twelve pieces of time-series data that are independent of each other and that are associated with the twelve sensitive membranes 13. The measurement result acquisition section 42 supplies the plurality of pieces of time-series data to the later-described odor identification section 43.

Further, the measurement result acquisition section 42 additionally supplies acquisition condition information to the odor identification section 43 in association with the twelve pieces of time-series data indicative of temporal changes in the resistance values of the sensitive membranes 13. The acquisition condition information identifies a data acquisition state indicating the degree of heating of specific types of sensitive membranes 13. The acquisition condition information includes information indicating the types of sensitive membranes 13 (indicating which of the plurality of sensitive membranes 13) and temperature information regarding the individual sensitive membranes 13. The temperature information regarding the individual sensitive membranes 13 may be information indicating the results of measurement by the temperature sensors 15, which are supplied from the heater drive circuit 16, or may be the heating instruction information (information indicating the operating conditions of the heaters 14 and the target temperatures of the sensitive membranes 13) which is designated for the gas sensor device 10 by the measurement result acquisition section 42.

The odor identification section 43 identifies the type and intensity of a currently presented odor by using the results of measurement by the gas sensor device 10, which are supplied from the measurement result acquisition section 42. As mentioned earlier, the data indicative of measurement results supplied from the measurement result acquisition section 42 is a combination of information indicating the type of sensitive membrane 13 (information associated with the type of sensitive material included in the sensitive membrane 13), information regarding the temperature of the sensitive membrane 13 (information indicating the degree to which the sensitive membrane 13 is heated by the corresponding heater 14), and time-series data indicating the temporal changes in the resistance value measured by the sensitive membrane 13. Sets of such combined information regarding all the sensitive membranes 13 (regarding the twelve sensitive membranes 13 in this instance) are parallelly supplied. The odor identification section 43 uses such sets of combined information to identify the type and intensity of an odor actually presented by the odor presentation apparatus 20.

Specifically, the odor identification section 43 inputs measurement result data, which is acquired by the measurement result acquisition section 42, to an identifier that is prepared in advance. The identifier is software for identifying the type and intensity of an odor according to various determination criteria. For example, based on information indicating, for example, what type of sensitive membrane 13 has undergone a change in the resistance value and the degree of change in each resistance value, the identifier identifies the type of odor presented by the odor presentation apparatus 20. Further, based on the amount of change in each resistance value, the identifier identifies the intensity of the identified odor. Note that the identifier may include a filter for performing various signal processing on time-series data, such as a noise reduction filter or a differential filter.

The contents of an identification algorithm to be executed by the identifier can be determined by pre-measuring the degree of reaction of a specific sensitive membrane 13 to each type of odor and compiling the results of such measurements into a database. Further, the identification algorithm of the identifier may be generated by machine learning. For example, a developer of the odor presentation system 1 uses the gas sensor device 10 to make measurements in a state where an odor whose type and intensity are known is presented by the odor presentation apparatus 20. Then, the developer inputs training data including information indicative of the type and intensity of the presented odor and time-series data indicative of the results of measurements, and performs machine learning. In this case, various machine learning algorithms may be used. For example, an algorithm of a recurrent neural network (RNN) for processing time-series data is applicable. When various types of odors are presented to perform such machine learning, it is possible to generate the identifier that is capable of identifying the type and intensity of an odor from the measurement results.

The software for implementing the identifier may be configured to be updatable. For example, in a case where the supply of a new cartridge begins to enable the odor presentation apparatus 20 to present a new type of odor, the developer generates the identifier capable of identifying the new type of odor, by using the earlier-described procedure, and supplies the generated identifier to the information processing apparatus 30. The information processing apparatus 30 is then able to identify a new odor by acquiring such a new identifier and updating the contents of the identifier stored in the storage section 32 of the information processing apparatus 30.

As described earlier, in the present embodiment, the gas sensor device 10 makes measurements by simultaneously using a plurality of types of sensitive membranes 13 that are formed of different types of sensitive materials. Further, the gas sensor device 10 simultaneously makes measurements in a state where a plurality of sensitive membranes 13 formed of sensitive materials of the same type are heated to different temperatures. By combining the results obtained by making parallel measurements under various different conditions as described above, the odor identification section 43 is able to accurately identify more types of odors than the number of types of sensitive membranes 13 included in the gas sensor device 10.

Further, the present embodiment identifies the type of odor by using the time-series data indicative of measurement results that are obtained by causing the gas sensor device 10 to repeatedly make measurements for a certain period of time. For example, even in a case where one sensitive membrane 13 reacts to both different types of odor molecules, sensor responsiveness may vary with the type of odor molecule. Accordingly, by identifying the type of odor through the use of time-series data indicating temporal changes in the resistance value of each sensitive membrane 13, the odor identification section 43 is able to achieve accurate identification in consideration of responsiveness and temporal changes in the reaction of each sensitive membrane 13 to the odor molecules.

Particularly, the odor identification section 43 may identify an odor according to data indicative of measurement results that are obtained after a timing at which control command output to the odor presentation apparatus 20 is started. More specifically, the odor identification section 43 acquires, from the odor presentation section 41, information indicative of the timing at which a control command is outputted to the odor presentation apparatus 20. Then, after the above-mentioned timing, the odor identification section 43 acquires time-series data indicative of the results of measurement by the gas sensor device 10. The acquired time-series data indicates temporal changes occurring in the resistance value after the timing at which odor presentation is started by the odor presentation apparatus 20.

Figure 4:
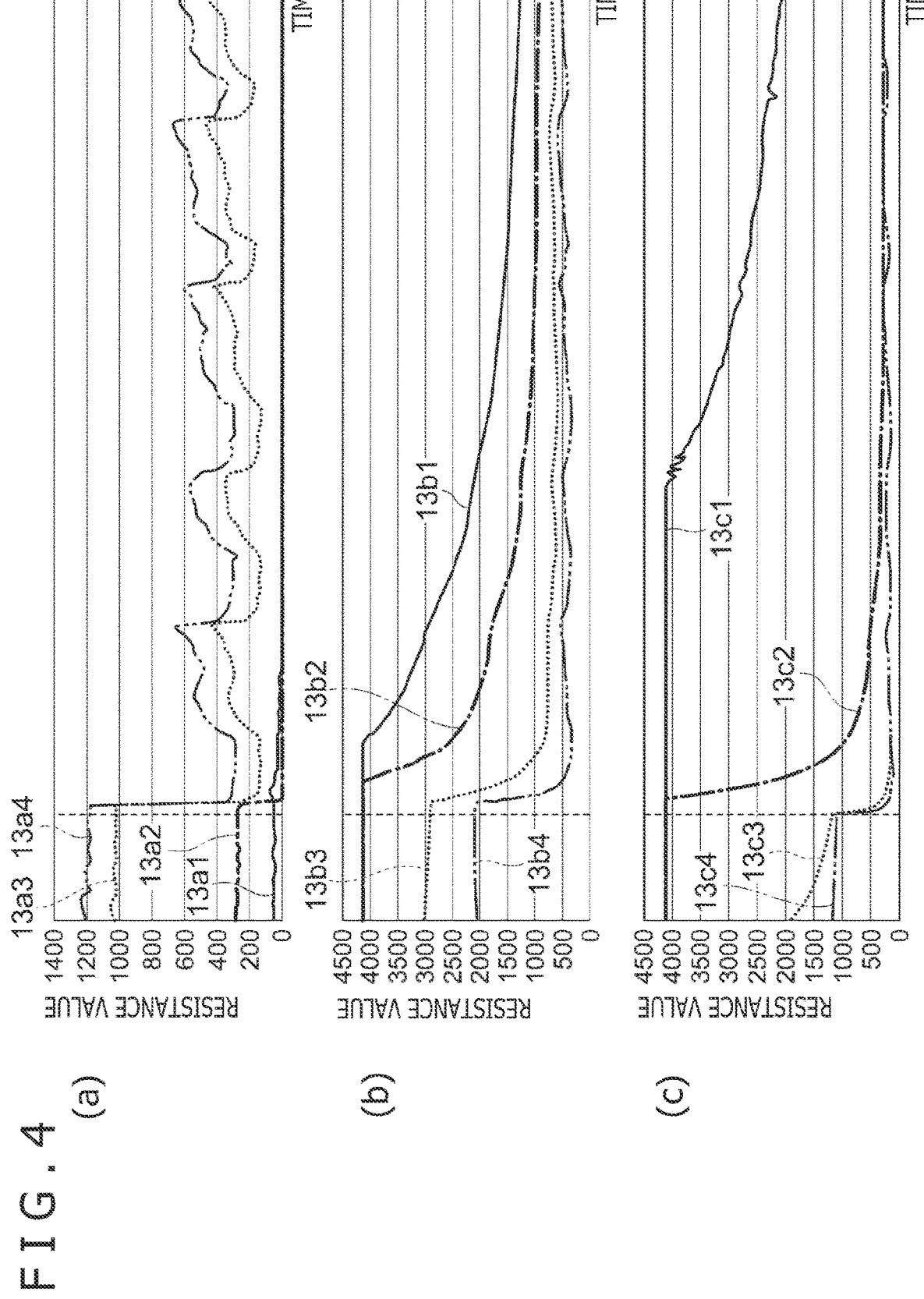
FIG. 4 illustrates diagrams of an example of a result of measurement by the gas sensor device.

FIGS. 4 and 5 illustrate example measurement results (indicative of temporal changes in the resistance value of each sensitive membrane 13) that are obtained by the gas sensor device 10 when a specific type of odor is presented. FIGS. 4 and 5 depict measurement results that are obtained when different types of odors are presented. FIGS. 4 and 5 each contain three graphs, and each of the three graphs relates to one type of sensitive membrane 13. Further, each graph depicts changes in the resistance values of four sensitive membranes 13 that are formed of sensitive materials of the same type. More specifically, the upper graph depicts the resistance values of the sensitive membranes 13*a*1 to 13*a*4, the middle graph depicts the resistance values of the sensitive membranes 13*b*1 to 13*b*4, and the lower graph depicts the resistance values of the sensitive membranes 13*c*1 to 13*c*4. Moreover, it is assumed that the sensitive membranes 13*a*1, 13*b*1, and 13*c*1 are heated to a target temperature T1, and that the sensitive membranes 13*a*2, 13*b*2, and 13*c*2 are heated to a target temperature T2, and further that the sensitive membranes 13*a*3, 13*b*3, and 13*c*3 are heated to a target temperature T3, and still further that the sensitive membranes 13*a*4, 13*b*4, and 13*c*4 are heated to a target temperature T4. Here, T1<T2<T3<T4. Note that, although it is assumed here that the sensitive membranes 13 of different types are heated to the same temperature, an alternative is to make measurements with the sensitive membranes 13 of different types heated to different temperatures.

As depicted in FIGS. 4 and 5, the type of presented odor determines the type of sensitive membrane 13 that reacts. Further, even in the case of sensitive membranes 13 of the same type, the resistance values vary by different amounts or remain almost unchanged depending on the temperature. Thus, different reactions occur. Further, not only the amount of change in the resistance values but also the reaction rate may vary with the type and temperature of the sensitive membrane 13. As depicted, for example, by the middle graph in FIG. 4, the resistance values of the sensitive membranes 13*b*3 and 13*b*4 heated to a high temperature decrease immediately after odor presentation. However, the resistance value of the sensitive membrane 13*b*2 begins to decrease with a slight delay, and the resistance value of the sensitive membrane 13*b*1 begins to decrease after a further elapsed time. Similarly, as depicted in the lower graph, the resistance values of the sensitive membranes 13*c*3 and 13*c*4 decrease immediately. However, the resistance value of the sensitive membrane 13*c*2 begins to decrease with a slight delay, and the resistance value of the sensitive membrane 13*c*1 remains unchanged for a relatively long period of time.

Accordingly, the odor identification section 43 identifies the type of odor according to the time-series data indicating the measurement result of each sensitive membrane 13 that is obtained after the timing at which odor presentation is started by the odor presentation apparatus 20. In this manner, the type and intensity of an odor can be identified with high accuracy in consideration of the aspect of response speed and temporal changes in the reaction of each sensitive membrane 13, which is caused by the odor released by the odor presentation apparatus 20.

The odor identification section 43 performs various processes by using the information regarding an odor identified by the above-described identifier. For example, the odor identification section 43 performs a comparison process of comparing information regarding the type and intensity of an odor specified by an instruction issued from the odor presentation section 41 to the odor presentation apparatus 20, with information regarding the type and intensity of an odor identified based on the results of measurement by the gas sensor device 10. In a case where the type of odor specified by the odor presentation section 41 is different from the type of identified odor, it is probable, for example, that the user has performed an erroneous operation by setting a wrong type of cartridge in the odor presentation apparatus 20. Therefore, based on the result of the comparison process, the odor identification section 43 may perform a process, for example, of displaying a warning to the user.

Meanwhile, in a case where the intensity of the measured odor is different from the intensity expected from the instruction issued by the odor presentation section 41, the odor identification section 43 may exercise feedback control in such a manner that the intensity of an odor presented by the odor presentation apparatus 20 approaches the expected intensity. For example, in a case where the intensity of an odor is lower than the expected intensity, the odor presentation section 41 instructs the odor presentation apparatus 20 to present a stronger odor. This makes it possible to perform real-time control in such a manner as to enable the odor presentation apparatus 20 to present the expected odor.

Further, in a case where the intensity of an odor identified by the odor identification section 43 is lower than a predetermined criterion or where the odor identification section 43 is unable to detect a specified odor presented by the odor presentation apparatus 20, it is conceivable that the amount of fragrance remaining in the cartridge set in the odor presentation apparatus 20 is small. In such a case, the odor identification section 43 may perform a process, for example, of displaying a prompt asking the user to replace the cartridge.

Further, in addition to the information regarding the type and intensity of an odor specified by the instruction issued to the odor presentation apparatus 20, the odor presentation section 41 may supply information indicating the number of times the type of odor supplied from the cartridge in the odor presentation apparatus 20 has been presented after cartridge replacement. When the information indicating the number of times the odor has been presented is used in combination with the results of measurement by the gas sensor device 10, the odor identification section 43 is able to more accurately detect a state where the remaining amount of fragrance is small.

Moreover, in a case where the intensity of an odor identified by the odor identification section 43 is lower than an expected value although cartridge replacement is made a short time ago (a state where the odor has been presented a small number of times after cartridge replacement) or where the measured amount of change in the resistance value of only a specific sensitive membrane 13 is, for example, smaller than an expected value, the intensity of an odor presented by the odor presentation apparatus 20 may not be lowered, but it is probable that a sensitive material forming the specific sensitive membrane 13 in the gas sensor device 10 is degraded. Therefore, in a case where the amount of change in the resistance value of a sensitive membrane 13 is found to be smaller than one expected from the instruction issued by the odor presentation section 41, the measurement result acquisition section 42 may correct the operating conditions of the heater 14 corresponding to the sensitive membrane 13 to raise the target temperature of the sensitive membrane 13. As a result, the sensitivity of the sensitive membrane 13 can be increased to continuously perform an odor identification process even in a case where the sensitive material is somewhat degraded. Note that the degree to which the target temperature needs to be corrected in the above-described example may be predefined in a database stored in the information processing apparatus 30.

Additionally, the odor presentation section 41 may not only transmit an instruction for terminating the presentation of odor to the odor presentation apparatus 20 but also convey information indicative of a timing for odor presentation termination to the odor identification section 43. When the information indicative of the timing for odor presentation termination is used, the odor identification section 43 is not only able to verify that a specified odor is presented by the odor presentation apparatus 20, but is also able to verify that the presentation of odor is terminated as specified.

The gas sensor device 10 according to the present embodiment, which has been described above, is configured such that various types of odors presented by the odor presentation apparatus 20 can accurately be identified by using the results of measurement provided by a plurality of sensitive membranes 13. Further, the odor presentation system 1 identifies, at a relatively high response speed, the type and intensity of an odor presented by the odor presentation apparatus 20, and is thus able to perform real-time control of the odor presented to the user and verify whether the odor is presented in a manner prescribed by the application program. This provides improved usability of the odor presentation apparatus 20.

The present invention is not limited to the foregoing embodiment. For example, the foregoing description assumes that the sensitive membranes 13 each include any of oxide semiconductor materials as the sensitive material reacting to molecules in the air. Alternatively, the sensitive membranes 13 may include a different semiconductor material or a different material reacting to the molecules in the air.

Further, the description of the foregoing embodiment assumes that the sensitive membranes 13 react to odor molecules causing an odor sensed by humans. Alternatively, the sensitive membranes 13 may react to other substances present in the air. For example, the odor presentation apparatus 20 may release odorless marker molecules in addition to the odor molecules causing an odor, and the sensitive membranes 13 of the gas sensor device 10 may be formed of a material reacting to such marker molecules. In such a case, the information processing apparatus 30 is able to estimate the type and intensity of an odor to be presented by the odor presentation apparatus 20, by measuring the type and amount of marker molecules.

REFERENCE SIGNS LIST

1: Odor presentation system
10: Gas sensor device
11: Sensor section
12: Control circuit
13: Sensitive membrane
14: Heater
15: Temperature sensor
16: Heater drive circuit
17: Measuring circuit
20: Odor presentation apparatus
30: Information processing apparatus
31: Control section
32: Storage section
33: Interface section
41: Odor presentation section
42: Measurement result acquisition section
43: Odor identification section

12

The invention claimed is:

1. A gas sensor device comprising:
a plurality of sensitive members that have respective sensitive materials reacting to molecules present in air and targeted for measurement, wherein at least two of the plurality of sensitive members include sensitive materials of a same type; and
a measuring instrument that independently measures the respective reactions of the plurality of sensitive members to the molecules.

2. The gas sensor device according to claim 1, wherein at least some of the plurality of sensitive members include sensitive materials of different types.

3. The gas sensor device according to claim 1, further comprising:
heaters that heat corresponding ones of the plurality of sensitive members and independently vary temperatures of the corresponding ones of the plurality of sensitive members.

4. The gas sensor device according to claim 3, wherein the measuring instrument makes the measurements in a state where a plurality of sensitive members including the sensitive materials of the same type are heated to different temperatures.

5. The gas sensor device according to claim 1, wherein the measuring instrument measures a change in a resistance value of each of the plurality of sensitive members at predetermined time intervals.

6. An information processing apparatus comprising:
an acquisition section that acquires respective results of measurements of a plurality of sensitive members from a gas sensor device, the gas sensor device including the plurality of sensitive members that have respective sensitive materials reacting to molecules present in air and targeted for measurement and a measuring instrument that independently measures the respective reactions of the plurality of sensitive members to the molecules; and
an identification section that, based on the acquired results of the measurements, identifies a type and intensity of an odor included in air.

7. The information processing apparatus according to claim 6, wherein
the information processing apparatus is connected to an odor presentation apparatus, and
the identification section performs a comparison process of comparing the identified type and intensity of the odor with an odor presentation instruction issued to the odor presentation apparatus.

8. The information processing apparatus according to claim 6, wherein
the acquisition section acquires not only the results of the measurements but also temperature data indicative of respective temperatures of the plurality of sensitive members at a time of the measurements, and
the identification section performs the identification by using the acquired temperature data.

9. The information processing apparatus according to claim 6, wherein
the acquisition section acquires time-series data indicative of temporal changes in the results of the measurements, and
the identification section performs the identification based on the temporal changes in the acquired results of the measurements.

10. The information processing apparatus according to claim 9, wherein the information processing apparatus is connected to an odor presentation apparatus, the acquisition section acquires time-series data indicative of temporal changes in the results of the measurements that is obtained after a timing at which odor presentation is started by the odor presentation apparatus, and the identification section identifies, based on the acquired temporal changes in the results of the measurements, a type and intensity of an odor presented by the odor presentation apparatus.

11. The information processing apparatus according to claim 10, wherein the identification section performs the identification by using a learned model, the learned model being obtained when machine learning is performed by using, as training data, the time-series data indicative of the temporal changes in the results of the measurements that is obtained after the timing at which the odor presentation is started and information indicative of the type of the odor presented by the odor presentation apparatus.

12. The information processing apparatus according to claim 10, wherein at least two of the plurality of sensitive members include sensitive materials of a same type.

13. The information processing apparatus according to claim 10, wherein the measuring instrument measures a change in a resistance value of each of the plurality of sensitive members at predetermined time intervals.

14. The information processing apparatus according to claim 10, wherein the respective results of measurements of the plurality of sensitive members comprises time-series data indicative of temporal changes in resistance values of the plurality of sensitive membranes.

15. An odor presentation system comprising:
an odor presentation apparatus that is able to present a plurality of types of odors;
a gas sensor device; and
an information processing apparatus,
the gas sensor device including
a plurality of sensitive members that have respective sensitive materials reacting to molecules present in air and targeted for measurement, and
a measuring instrument that independently measures the respective reactions of the plurality of sensitive members to the molecules, and
the information processing apparatus including
an acquisition section that acquires respective results of measurements of the plurality of sensitive members in a situation where an odor is presented by the odor presentation apparatus, and
an identification section that, based on the acquired results of the measurements, identifies a type and intensity of the odor presented by the odor presentation apparatus.

16. The odor presentation system according to claim 15, wherein at least two of the plurality of sensitive members include sensitive materials of a same type.

17. The odor presentation system according to claim 15, wherein the measuring instrument measures a change in a resistance value of each of the plurality of sensitive members at predetermined time intervals.

18. The odor presentation system according to claim 15, wherein the respective results of measurements of the plurality of sensitive members comprises time-series data indicative of temporal changes in resistance values of the plurality of sensitive membranes.

* * * * *